United States Patent [19]

Fletcher et al.

[11] 4,014,745

[45] Mar. 29, 1977

[54] APPLICATION OF LUCIFERASE ASSAY FOR ATP TO ANTIMICROBIAL DRUG SUSCEPTIBILITY

[76] Inventors: James C. Fletcher, Administrator of the National Aeronautics and Space Administration, with respect to an invention of; Emmett W. Chappelle, Baltimore; Grace L. Picciolo, Tantallon, both of Md.; Hillar Vellend, Newton Upper Falls, Mass.; Stephanie A. Tuttle, Watertown, Mass.; Michael J. Barza, Boston, Mass.; Louis Weinstein, Newtonville, Mass.

[22] Filed: Apr. 30, 1975

[21] Appl. No.: 572,991

[52] U.S. Cl. ................. 195/103.5 K; 195/103.5 R
[51] Int. Cl.$^2$ ........................................ C12K 1/04
[58] Field of Search ............................ 195/103.5 R
[56] References Cited
UNITED STATES PATENTS 3,745,090  7/1973   Chappelle et al. ......... 195/103.5 R
3,772,154  11/1973  Isenberg et al. ........... 195/103.5 R
3,940,250  2/1976   Plakas et al. ............... 195/103.5 R

*Primary Examiner*—A. Louis Monacell
*Assistant Examiner*—C. A. Fan
*Attorney, Agent, or Firm*—Ronald F. Sandler; John R. Manning

[57] ABSTRACT

The susceptibility of bacteria, particularly those derived from body fluids, to antimicrobial agents is determined in terms of an ATP index measured by culturing a bacterium in a growth medium, assaying the amount of ATP in a sample of the cultured bacterium by measuring the amount of luminescent light emitted when the bacterial ATP is reacted with a luciferase-luciferin mixture, subjecting the sample of the cultured bacterium to an antibiotic agent and assaying the amount of bacterial adenosine triphosphate after treatment with the antibiotic by measuring the luminescent light resulting from the reaction, whereby the ATP index is determined from the values obtained from the assay procedures.

15 Claims, No Drawings

APPLICATION OF LUCIFERASE ASSAY FOR ATP TO ANTIMICROBIAL DRUG SUSCEPTIBILITY

ORIGIN OF THE INVENTION

The invention described herein was made in the performance of work under a NASA Contract and is subject to the provisions of Section 305 of the National Aeronautics and Space Act of 1958, Public Law 85—568 (72 Stat. 435; 42 USC 2457).

BACKGROUND OF THE INVENTION

1. Field of the Invention:

The present invention relates to a method for rapidly determining the effectiveness of antimicrobial agents against bacteria. More particularly, the invention relates to a method for rapidly determining the effectiveness of antimicrobial agents against bacteria by measuring the amount of adenosine triphosphate (ATI) isolated from the bacteria remaining after treatment with the antimicrobial agent.

2. Description of the Prior Art:

A rapid and routine procedure for the determination of the effectiveness of antimicrobial agents against various bacteria is very frequently of vital importance, particularly for the rapid measurement of the effectiveness of antimicrobial agents against bacteria in urine. Present techniques for the determination of microbial susceptibility generally require overnight incubation of an infecting organism after its isolation.

Thus, generally a minimum of 48 hours is required to test the effectiveness of antimicrobial agents after a specimen is received in the laboratory. The most commonly used conventional techniques for the determination of microbial susceptibility to antimicrobial agents include agar diffusion (Kirby-Bauer technique), broth dilution and agar dilution. A long-standing need continues to exist for a rapid means for determining microbial sensitivity to antimicrobial agents to avoid the inclusion of inappropriate, unnecessary, and often toxic agents in the therapeutic regimen of an infected person.

The conventional broth dilution method (MIC-Broth Dilution) of determining microbial sensitivity to antimicrobial agents involves visual detection of the least amount of antimicrobial agent required to cause complete inhibition of bacterial growth in a culture medium. In the technique, two-fold dilutions of antibiotics are made in a suitable culture medium. A control tube containing the culture medium, but no antibiotic is also included for each organism tested. The organism is then allowed to grow to a logarithmic or early stationary phase of growth in the medium, and then diluted to a solution containing $10^4$ to $10^5$ viable units per milliliter. A quantity of the cultured medium is then placed in each tube of a series containing varying amounts of an antibiotic, and the tubes are allowed to incubate at 37° C for 16 to 20 hours. Thereafter, the end point of the test is determined visually, as mentioned above. A disadvantage of this technique besides the relatively very long time required to complete the test, is that care must be taken to recognize that slight amounts of turbidity present may be caused by the inoculum itself and not by the growth of the organism.

The Kirby-Bauer method involves an agar diffusion technique for the measurement of microbial susceptibilities. In the test an inoculum of an organism, which is an overnight culture, is prepared by diluting the inoculum in trypticase soy broth to such a concentration that a dense, but not confluent growth is observed. The culture turbidity is adjusted to a concentration which conforms to a turbidity standard. The standard is formed by mixing 0.5 ml of 0.048 M barium chloride (1.175% w/v $BaCl \cdot 2H_2O$) with 99.5 ml of 0.36 $NH_2SO_4$ (1% w/v). A cotton swab is then soaked in the diluted culture, and an agar plate is then streaked in four directions to obtain an even and thorough distribution of the organism on the plate. The treated plates are dried for 15 minutes at 37° C. Thereafter, antibiotic discs are applied to the surface of the agar and pressed into place. No more than 12 discs are used per plate to prevent overlapping of zones. The plates are then allowed to stand at room temperature for 30 minutes and incubated at 37° C for 18 to 20 hours. The end point is shown by a clearly defined zone around the antibiotic disc where no growth has occurred. The zone is measured and compared with the given sensitivity or resistance of the antibiotic. Only a zone having a diameter greater than 6.0 mm is significant because the antibiotic discs are 6.0 mm in diameter. The chief disadvantage of the diffusion technique is the long period of time required to obtain the microbial sensitivity results.

SUMMARY OF THE INVENTION

Accordingly, one object of the present invention is to provide a rapid method for determining the sensitivity of bacterial organisms to antimicrobial agents.

Another object of the invention is to provide a method of determining the sensitivity of bacterial organisms to antimicrobial agents by utilizing a bioluminescent reaction involving bacterial adenosine triphosphate (ATP) and a mixture of luciferase and luciferin.

Yet another object of the invention is to provide a method of measuring the sensitivity of microbial organisms present in urine to various antimicrobial agents.

Briefly, these objects and other objects of the invention, as hereinafter will become more readily apparent, can be attained by a method for determining the sensitivity of bacteria to antimicrobial agents by measurement of an ATP index by culturing a bacterium in a growth medium; assaying the amount of bacterial adenosine triphosphate in a sample of said cultured bacterium by measuring the amount of luminescent light emitted when said bacterial adenosine triphosphate is reacted with a luciferase-luciferin mixture; subjecting said sample of said cultured bacterium to an antibiotic agent; and assaying the amount of bacterial adenosine triphosphate after treatment with said antibiotic by measuring the luminescent light resulting from said reaction; whereby the ATP index is determined from the values obtained from said assay procedures.

DETAILED DESCRIPTION OF THE PREFERRED EMBODIMENTS

Adenosine triphosphate (hereinafter referred to as ATP) is a component of all cellular matter, thereby making it an excellent indicator of the presence of various life forms. A very sensitive test for the presence of ATP is an enzymatic bioluminescent assay. The test is accomplished by reacting ATP with the enzyme luciferase and luciferin in the presence of a divalent metal ion such as magnesium or manganese.

It has previously been shown that the concentration of ATP derived from several bacteria strains from pure cultures can be closely correlated to a bacterial count. This correlation is described by E. W. Chappelle and G. V. Levin in "Use of the Firefly Bioluminescent Reaction for Rapid Detection and Counting of Bacteria" as described in "Biochemical Medicine", 2, 41–52 (June,1968), and the article is incorporated herein by reference. By using this technique on a number of bacterial species, an average ATP content of a bacterial cell has been established as about $3 \times 10^{-10}$ μ g, i.e., from $0.28 \times 10^{-10}$ μ g to $8.9 \times 10^{-10}$ μ g.

In the adaption of this technique for the detection of bacteria in urine, a method first had to be developed to separate non-bacterial sources of ATP from the bacteria. Typical non-bacterial sources of ATP in urine include free soluble ATP and the ATP present in red and white blood cells. The separation process involves treating a urine sample with a non-ionic detergent which ruptures any red and white blood cells present, thus releasing ATP into solution in a freely soluble form. The freed non-bacterial ATP is then hydrolyzed with an ATP hydrolyzing enzyme, i.e., an ATPase, and thereafter the ATPase is denatured by heating or by some chemical means.

Bacterial ATP can now be released after removal of non-bacterial ATP by rupturing the bacterial cells by the addition of acid. Subsequently, the solution is neutralized, and the pH and ionic strength of the urine sample is adjusted by a buffer for optimum luciferase activity. The solution is then treated with a luciferin-luciferase mixture, and if ATP is present, light is emitted from the ensuing bioluminescent reaction and is detected and recorded by an appropriate apparatus. The following is believed to be the reaction sequence by which light is emitted by the reaction of ATP with luciferase-luciferin. This is the same reaction which occurs when fireflies emit their characteristic light.

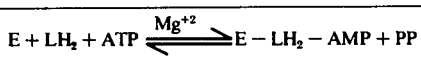

E = luciferase
LH$_2$ = reduced luciferin
ATP = adenosine triphosphate
AMP = adenosine monophosphate
PP = pyrophosphate
T = thiazolinone
hν = Light at 550 nm If all of the components of the above reaction are maintained in a concentration in excess of the ATP, the emission of light is directly proportional to the amount of ATP introduced. This allows a direct correlation between the magnitude of light emission and ATP concentration, when a treated urine sample is combined with the luciferase-luciferin mixture and when a standard curve is prepared. This detection mechanism was adapted for an accurate technique of determining bacterial levels in urine as described in U.S. Pat. No. 3,745,090 and is herein incorporated by reference.

The present invention resides in the adaptation of the bioluminescent reaction of luciferase-luciferin with ATP for the rapid determination of microbial sensitivity to antimicrobial agents. The method of the invention is effective for determining the sensitivity of bacteria isolated from various body fluids, particularly from urine. The measurement of adenosine triphosphate for determining microbial sensitivities to antibiotics was selected because (1) the substance is present in all viable microorganisms; (2) the concentration of ATP in bacteria is directly related to fundamental processes of oxidative phosphorylation and respiration; (3) although none of the commonly used antimicrobial agents act directly on oxidative phosphorylation and respiration of the organisms, it is evident that the antimicrobial agents may have profound, indirect consequences on the ATP content of bacteria and thus their rate of growth; and (4) the measurement of ATP by the luciferase bioluminescence reaction is precise, reproducible and compatible with automation.

In the present process of measuring microbial sensitivity, a sample of a body fluid such as urine, lymph fluid, plasma, blood, spinal fluid, saliva, mucus, ascites and the like is cultured. Normally, from 0.01 to 1.0 ml of a body fluid specimen is cultured. The amount of specimen to be cultured is not a critical factor. Many types of conventional culture media can be used with the nutrients either in agar or a liquid medium. (See Bailey and Scott, *Diagnostic Microbiology*, Third Edition, C. V. Mosby Co.,1970). The selection of a particular culture medium is a matter of choice and is not a critical factor. Culturing of the specimen is normally accomplished from 8 – 96 hours at temperatures ranging from 20° to 45° C. Each individual bacterial colony produced which is recognized as being different is isolated, and then placed in a separate culture broth, again for about 16 to 48 hours. The method by which the bacterial colony is isolated is not critical and can be accomplished by such techniques as a metal loop or by a differential media. With the differential media technique, for instance, gram-positive bacteria are mixed with gram-negative bacteria. The mixed bacteria are grown in a phenylalanine agar medium to inhibit the gram-negative bacteria and to enhance the growth of the gram-positive bacteria.

A fresh sample of bacterial culture is then diluted in a broth to obtain a uniform inoculum of about $10^4$ to $10^8$ CFU/ml, preferably $10^6$ CFU/ml. (The abbreviation "CFU" refers herein to colony forming units.) Each broth culture is then preincubated at 20° to 45° C to initiate growth of the bacterial strain.

The antibiotic solutions used to treat the cultured bacteria are formulated by diluting an antibiotic solution to an appropriate concentration, which depends only on the useful range of each antibiotic, with water or a saline solution. Usually, the concentration of antibiotic in solution ranges from 0.1 – 100μ gm/ml. The salt concentration of the saline solution can assume any value that is not detrimental to the bacteria. Normally, however, the saline solutions are about 0.9% solutions. Suitable antibiotics used in the present process include ampicillin trihydrate, tetracycline hydrochloride, potassium penicillin G, sodium cephalothin, erythromycin base, sodium colistimethate, nitrofurantoin, sodium nafcillin, sodium ampicillin, nalidixic acid, chloramphenicol, disodium carbenicillin, gentamicin sulfate, clindamycin phosphate, and sulfisoxazole. Other antibiotics can also be used. The only requirement is that the antibiotic used should give a good correlation.

At this point in the procedure a sample of the broth culture is placed into a receptacle containing the particular antibiotic to be tested. The amount of antibiotic used relative to the culture varies as a function of the particular antibiotic used. Normally, from about 0.1 ml to 10 ml of a culture specimen is added to the antibiotic solution. Simultaneously, a sample of broth culture is added to two separate receptacles containing a 0% to 2% saline solution. This forms duplicate control samples. The amount of saline solution added to each control sample equals the volume of the antibiotic added to the sample with same. One of the control samples is assayed by the ATP-luciferase technique to establish a bacterial count at time zero. Thereafter, the other control sample and the test sample with the antibiotic are incubated for 0.5 to 10 hours at 20° to 45° C. This incubation temperature range will allow for comparison for growth at body temperature. In the final step of the procedure, the later control sample and the test sample with the antibiotic are assayed, again by the ATP-luciferase technique, to determine the sensitivity of the particular bacterium used to the particular antibiotic under test. It should be clearly understood that many types of bacteria may be simultaneously tested with many types of antibiotics.

The assay technique is accomplished by first placing a culture sample in a sterile receptacle suitable for centrifuging. Usually, a minimum of about 0.1 ml to a maximum amount of about the capacity of the receptacle or about 15 ml, preferably 10 ml, of the culture sample is placed in the receptacle. Scrupulous procedures must be followed to avoid contamination by extraneous ATP sources. The sample containers must be thoroughly cleaned, for instance, by acid washing, because residual ATP readily clings to glass surfaces. Further, the deionized, distilled water should be used in preparing all reagents. Many commercial detergents will interefere with the assay so that all glassware used must be scrupulously free of residue.

The test solutions are now ready for the removal of all non-microbial sources of ATP which are present in the original specimen. This is accomplished by treating the test solutions containing the cultured organism with an ATPase. An ATPase hydrolyzing solution is formed by mixing a calcium salt, a surfactant and ATPase. The function of the surfactant is to rupture all non-bacterial cells in solution and free all non-bacterial adenosine triphosphate into solution. Any convenient means can be used to rupture the non-bacterial cell as long as the bacterial cells are not detrimentally affected. A convenient manner of rupturing the non-bacterial cells is to reduce the surface tension of the non-bacterial cells.

It has been found that certain surfactant compounds, which effectively lower the surface tension of aqueous solution, also readily rupture non-bacterial cells. Suitable surfactants include cationic surfactants, anionic surfactants and nonionic surfactants such as octyl phenoxy polyethoxyethanols (Triton-X100). Other types of surfactants include triterpenoid saponins, steroid saponins, sulfosuccinates such as dioctyl sodium sulfo-succinates, various glycosides and some polyoxyethylene derivatives of fatty acid partial esters of sorbitol anhydrides. The concentration of surfactant in solution varies and can be any amount which achieves a surface tension of about 20 – 40 dynes /cm at 25° C in $H_2O$.

The concentration of ATPase in the hydrolyzing solution varies. The only requirement is that the minimum amount used should promote hydrolysis of 1 $\mu$ mole of ATP in about 15 minutes. Suitable sources of ATPase for the ATPase solution include potato apyrase, insect apyrase, muscle ATPase, liver ATPase, and the like. More preferred as a hydrolyzing agent is potato apyrase since it is more completely characterized, easily purified, easily obtained and yields excellent results. In this hydrolyzing solution, any convenient calcium salt can be used as long as the anion does not have an inhibitory effect such as calcium chloride, calcium bromide, calcium iodide, calcium sulfate and the like, such that a calcium ion concentration ranging from $5 \times 10^{-4}$ M to $5 \times 10^{-3}$ M is achieved. The presence of calcium ion is essential as a catalyst because it is a required cofactor for apyrase.

After the ATPase solution is added to the bacteria-containing solution, the sample is allowed to stand at ambient temperature for sufficient time to permit complete hydrolysis, preferably from 1 to 25 minutes, more preferably from 5 to about 15 minutes.

After removal of all non-microbial sources of ATP, the hydrolyzing ATPase enzyme solution is denatured or destroyed and simultaneously the bacterial cells are ruptured which releases the ATP in the cells. This is usually accomplished by physical or chemical means. Suitable chemical agents include acids such as nitric acid, phosphoric acid, sulfuric acid, perchloric acid, hydrochloric acid, and the like; organic acids, such as formic acid, acetic acid, and the like; bases such as alkali metal and alkaline earth metal hydroxides and carbonates, organic bases such as pyridine; organic solvents such as acetone, methylene chloride, chloroform and the like. The important feature is that rupture of the bacterial cell walls does not occur and destroy bacterial ATP. Physical means of denaturing include heat and short wavelength radiation. It has been found that heating the test solution for a brief period, i.e., about 1 to 15 minutes, preferably about 5 to 12 minutes, from 60° to 100° C is effective to denature the hydrolyzing enzyme.

It is easily seen that an entire range of compounds and procedures may be used to effect the inactivation or denaturation of the hydrolyzing enzyme, requiring only that they do, in fact, destroy the activity thereof without appreciably affecting the bacterial cells or the bioluminescent reaction used to determine the bacterial ATP. Any compound used which is toxic to the luciferase-ATP reaction would ultimately have to be removed or neutralized.

The denaturation of the hydrolyzing enzyme is generally carried out at an elevated temperature, preferably 95° C, and ambient pressure; however, if it should be more convenient or necessary to carry this out at elevated pressures, there is no apparent reason for not doing so.

After bacterial ATP has been released in solution, the test solution is diluted with water to raise the pH of the same to about 1.8 – 2.9, preferably 2.1, if an acid is used to denature the ATPase, and then vortexed to mix the solution. Thereafter, the test solution is treated with a solution containing a luciferase-luciferin mixture, and the light which is emitted is measured in a luminescence photometer in order to measure the ATP index. The pH of the final solution containing bacterial ATP and luciferase is that which is sufficient for the bioluminescent reaction to occur, usually from 6.5 to 8.5, preferably 7.4 to 8.0, most preferably 7.75. A buffer is present in the solution to adjust the ionic strength as well as keep the pH within the appropriate range. The amount of buffer added is within the range of about 0.05 ml to about 1.0 ml at a concentration of about 2 to 2.5 M. Suitable buffers include TES buffer [N-tris (hydroxymethyl)methyl-2-amino-sulfuric acid]; phosphate buffers, arsenate buffers; Tris buffers, e.g., tris (hydroxymethyl)aminomethane; arsine buffers; glycylglycine buffer; and N-2-hydroxyethylpiperazine-N-2-ethanesulfonic acid buffer. Also present in the luciferase-luciferin mixture can be any soluble manganese or magnesium salt. Any manganese or magnesium salt containing an anion which has an inhibitory effect should not be used. Usually, the mixture contains from 0.1 mg – 100 mg/ml of luciferin, preferably 0.7 M luciferin. It is readily apparent that the receptacle which contains the control bacterial sample will emit the greatest amount of luminescent light because no antibiotic has been present in the control sample to diminish the amount of bacteria present. The antibiotic containing solutions will emit lesser amounts of luminescent light if there is an adverse influence of the antibiotic on the growth of the bacteria. The bioluminescent readings are normally conducted at room temperature in a photometer and the ATP index is calculated according to the following formula:

$$\text{ATP index} = \frac{B_t - A_o}{A_t - A_o},$$

wherein $B_t$ represents the light reading obtained for a solution of cultured broth which is treated with an antibiotic and then allowed to incubate, $A_t$ represents the light reading obtained for a solution of cultured broth (control sample) which is allowed to incubate without the presence of antibiotic, and $A_o$ represents the light reading obtained for a solution of cultured broth (control sample) at time zero which is not incubated nor treated with antibiotic. The interpretation of the results obtained by the light measurements is as follows: Those samples of antibiotic treated cultures having an ATP index $>+\ 0.05$ are deemed as resistant bacterial samples, while those samples of antibiotic treated cultures having an ATP index $+\ 0.05$ are deemed as sensitive bacterial samples.

An alternative method of calculating the ATP index is to use the following logarithmic relationship:

$$\text{ATP index} = \frac{\log B_t - \log A_o}{\log A_t - \log A_o}$$

This formula was used to obtain the data in the examples. According to the logarithmic formula, antibiotic treated cultures having an ATP index value $>+\ 0.25$ are deemed as resistant bacterial samples, while those samples of antibiotic treated cultures having an ATP index $+\ 0.25$ are deemed as sensitive bacterial samples. However, in determining the ATP index for a certain antibiotic-bacteria combination, it is recommended that the logarithmic method should not be used. Rather, the non-logarithmic formula is the method of choice and should be used to determine all ATP index values.

The examples which follow show the reproducability of the ATP index results of the following bacterial cultures which are representative of the types of bacteria to which the present method is applicable. Suitable bacteria include *Escherichia coli, Staphylococcus aureus, Klebsiella aeogenes, Enterobacter cloacae, Serratea marcescens, Proteus vulgaris, Pseudomona aerugenosa, Proteus mirabilis, Providencia stuartii, Staphylococcus epidermidis and Enterococcus.*

The invention is further illustrated by the following examples in which all parts and percentages are by weight unless otherwise indicated. These examples are illustrative of results obtained with one embodiment of the invention and are provided to teach those skilled in the art how to practice the invention and to represent one mode contemplated for carrying out the invention.

PREPARATION OF BACTERIAL STRAINS

Bacterial strains were maintained on trypticase Soy Agar slants at 4° C. At monthly intervals, fresh broth cultures were streaked onto 5% sheep's blood agar and esoin methylene blue agar to confirm the purity of the sample. Five similar colonies from the blood agar were inoculated into fresh broth from which new agar slants were prepared. Agar diffusion sensitivity tests were done periodically on the bacterial strains to confirm the stability of their susceptibility patterns.

PREPARATION OF STOCK ANTIBIOTIC SOLUTIONS

Stock solutions of the antibiotics shown in Tables 1 and 3 were prepared by mixing each antibiotic into a volume of sterile, distilled water to a concentration of 1280 $\mu$ g/ml and each solution was dispensed into sterile, capped polypropylene tubes (12 × 75 mm) using a Cornwall syringe pipette having a 0.22 micron Millepore filter. In the preparation of antibiotic solutions of sulfisoxazole, erythromycin base, nitrofuranoin and nalidixic acid, special solvents of 10% sodium hydroxide, ethanol, dimethylformamide and 1 N sodium hydroxide were used. The solutions were frozen at $-20°$C for at most two weeks and were used within one hour of being thawed.

The antibiotics studied and the concentrations used to determine the ATP index relative to a specific bacterium are shown in Table 1. The concentration of antibiotic selected was determined empirically by measuring the effect of the mean inhibitory concentration (MIC) breakpoints generally quoted for the agar diffusion method on a spectrum of known organisms. The concentrations shown in Tables 1 – 4 fall somewhere in between the MIC breakpoints.

PREPARATION OF A BODY FLUID SAMPLE FOR ATP INDEX MEASUREMENT

A fresh sample of an overnight broth culture of a urine specimen which was cultured on a blood agar plate was diluted 1000-fold in Trypticase Soy Broth at 37° C, whereby an inoculum of approximately $10^6$ colony forming units (CFU/ml) was obtained. The inoculum was preincubated at 37° C for 30 minutes and 4.5 ml of the incubated inoculum was placed in two tubes, one of which contained 0.5 ml of sterile 0.9% sodium chloride (control sample) and the other contained 0.5 ml of an antibiotic solution in 0.9% sodium chloride to yield the final concentration shown in Tables 1 – 4. (Tables 1 – 4 also show the specific antibiotics tested). A one-half ml quantity of the control sample was immediately assayed for ATP ($A_o$) as described specifically below. Both the control sample and the antibiotic sample were incubated at 37° C for 2.5 hours. After incubation, 0.5 ml samples from each tube were assayed for ATP ($A_t$ and $B_t$ values).

ATP ASSAY FOR THE DETERMINATION OF THE ATP INDEX

Preparation of ATPase Hydrolysis Solution:

To a solution of 0.3 M calcium chloride containing 0.6% Triton X-100 kept frozen at $-20°$ C in aliquots suitable for a day's work was added 5 mg of ATPase (Apyrase, Grade 1, Sigma) per milliliter immediately before an assay and gently mixed by inversion.

Preparation of Luciferase-Luciferin Mixture:

The contents of a vial of luciferase (Luminescence Biometer Reagent Kit, DuPont Instruments) was reconstituted with 1.5 ml of 0.2 M TRIS (Trizma base, Sigma) containing 0.01 M magnesium sulfate at a pH of 8.4. This solution was also kept frozen in suitable aliquot sizes. After complete solution of the mixture, 0.1 ml of the reagent was dispensed into reaction cuvettes.

The actual assays were conducted as follows. A 0.5 ml sample of a broth culture was placed in a sterile polypropylene tube. To the culture was added 0.1 ml of the ATPase hydrolysis solution, which was then vortexed and allowed to stand for 15 minutes. By this procedure, all non-bacterial ATP in solution was denatured or destroyed. Thereafter, 0.1 ml of 1.5 N $HNO_3$ was added to the denatured broth, and the tube was vortexed and allowed to stand for 5 minutes. This procedure released ATP from the bacterial cells present in the culture. The acid solution was then diluted with 4.3 ml of sterile, deionized water (Travenol). Thereafter, 0.1 ml of the diluted broth was withdrawn into a disposable tuberculin syringe and then injected into a working sample of the luciferase-luciferin mixture. Luminescent readings were then taken in a Luminescence Biometer, DuPont Instruments, which was standardized to $1.0 \times 10^8$ femtograms (fg) ATP/ml of the original sample by adding 0.05 ml of a freshly thawed ATP standard (0.1 $\mu$ g/ml) to the final reaction volume of a blank tube, i.e., a sterile broth. The ATP index of each culture-antibiotic solution tested was then calculated by the formula shown above.

KIRBY-BAUER AGAR DIFFUSION SENSITIVITY TEST

Agar diffusion sensitivity testing was conducted by the tentative standards recommended by the National Committee for Clinical Laboratory Standards Subcommittee on Antimicrobial Susceptibility Testing.

MIC-BROTH DILUTION TEST

This assay procedure was accomplished in a trypticase Soy Broth according to the method proposed by the International Collaborative Study on Antibiotic Susceptibility Testing.

The data in Tables 1 – 3 show the ATP indexes for each antibiotic-bacterium combination investigated. Also shown are the results for the same bacterium-antibiotic combinations as tested for sensitivity by the conventional Kirby-Bauer agar diffusion technique and the conventional MIC tube dilution techniques. The number of disagreements between the results of the present process and the Kirby-Bauer technique are summarized in Table 4.

TABLE 1

COMPARISON OF RESULTS OBTAINED BY ATP INDEX, AGAR DIFFUSION (KIRBY-BAUER), AND TUBE DILUTION MIC

MICROORGANISM

| ANTIBIOTIC ($\mu$g/ml) | Staphylococcus aureus ATCC 25923 | | | | Staphylococcus aureus S-187 | | | | Staphylococcus epidermidis 05995 | | | |
|---|---|---|---|---|---|---|---|---|---|---|---|---|
| | K-B (mm.) | MIC ($\mu$g/mg) | ATP INDEX | INTERPR. | K-B (mm.) | MIC ($\mu$g/ml) | ATP INDEX | INTERPR. | K-B (mm.) | MIC ($\mu$g/ml) | ATP INDEX | INTERPR. |
| PENICILLIN G (8) (0.15) | 32.5 | <0.125 | −0.86 −0.70 | S S | ND 14.5 | ND ND | ND +0.53 | ND R | 21 | 1.0 | −0.46 | S |
| AMPICILLIN (8) | 31 | <0.125 | −0.17 | S | ND | ND | ND | ND | 25 | 0.5 | −0.02 | S |
| NAFCILLIN (0.6) | 19.5 | ND | −0.79 | S | 19.5 | ND | −0.39 | S | ND | ND | ND | ND |
| CARBENICILLIN (128) | ND | ND | ND | ND | ND | ND | ND | ND | ND | ND | ND | ND |
| CEPHALOTHIN (16) | 32.5 | <0.125 | −0.38 | S | ND | ND | ND | ND | 35 | 0.25 | −0.24 | S |
| TETRACYCLINE (6) | 25.5 | 0.5 | −0.13 | S | ND | ND | ND | ND | 0 | >128 | +1.01 | R |
| ERYTHROMYCIN (4) | 28 | 0.25 | 0.00 | S | ND | ND | ND | ND | 29.5 | 0.25 | +0.08 | S |
| CLINDAMYCIN (2) | 26 | <0.25 | −0.26 | S | ND | ND | ND | ND | 29 | <0.125 | −0.01 | S |
| GENTAMICIN (6) | 24 | 0.25 | −0.07 | S | ND | ND | ND | ND | 30 | 0.125 | +0.04 | S |
| NITROFURANTOIN (50) | 18.5 | 16 | −0.05 | S | ND | ND | ND | ND | 25 | 4 | −0.12 | S |
| COLISTIN (8) | 0 | >128 | +0.88 | R | ND | ND | ND | ND | 0 | >128 | +0.91 | R |
| CHLORAMPHENICOL (12.5) | 24 | 4 | −0.28 | S | ND | ND | ND | ND | 27.5 | 4 | −0.24 | S |

ND = Not Done

TABLE 2

COMPARISON OF RESULTS OBTAINED BY ATP INDEX, AGAR DIFFUSION (KIRBY-BAUER), AND TUBE DILUTION MIC

MICROORGANISM

| ANTIBIOTIC ($\mu$g/ml) | Escherichia coli ATCC 25922 | | | | Klebsiella 07220 | | | | Enterobacter 05248 | | | |
|---|---|---|---|---|---|---|---|---|---|---|---|---|
| | K-B (mm.) | MIC ($\mu$g/ml) | ATP INDEX | INTERPR. | K-B (mm.) | MIC ($\mu$g/ml) | ATP INDEX | INTERPR. | K-B (mm.) | MIC ($\mu$g/ml) | INDEX | INTERPR. |
| PENICILLIN G (8) | 0 | 80 | +0.99 | R | 0 | >80 | +0.99 | R | 0 | >80 | +1.00 | R |
| AMPICILLIN (8) | 19 | 8 | −0.33 | S | 0 | >128 | +0.93 | R | 0 | >128 | +0.93 | R |
| NAFCILLIN (0.6) | ND | ND | ND | ND | ND | ND | ND | ND | ND | ND | ND | ND |
| CARBENICILLIN | 28 | 32 | −0.27 | S | ND | ND | ND | ND | ND | ND | ND | ND |

TABLE 2-continued

COMPARISON OF RESULTS OBTAINED BY ATP INDEX, AGAR DIFFUSION (KIRBY-BAUER), AND TUBE DILUTION MIC

| | MICROORGANISM | | | | | | | | | | |
|---|---|---|---|---|---|---|---|---|---|---|---|
| | Escherichia coli ATCC 25922 | | | | Klebsiella 07220 | | | | Enterobacter 05248 | | |
| ANTIBIOTIC (μg/ml) | K-B (mm.) | MIC (μg/ml) | ATP INDEX | INTERPR. | K-B (mm.) | MIC (μg/ml) | ATP INDEX | INTERPR. | K-B (mm.) | MIC (μg/ml) INDEX | INTERPR. |
| CEPHALOTHIN (16) | 19 | 32 | −0.30 | S | 21 | 16 | −0.46 | S | 0 | >128 +0.97 | R |
| TETRACYCLINE (6) | 20 | 4 | +0.13 | S | 19 | 8 | +0.07 | S | 19 | 8 +0.04 | S |
| ERYTHROMYCIN (4) | 10.5 | 64 | +0.92 | R | 11.0 | 128 | +0.98 | R | 0 | >128 +0.98 | R |
| CLINDAMYCIN (2) | 0 | 128 | +0.96 | R | 0 | >128 | +0.94 | R | 0 | >128 +0.94 | S |
| GENTAMICIN (6) | 22 | 4 | −0.43 | S | 22 | 2 | −0.39 | S | 24 | 2 −0.40 | S |
| NITROFURANTOIN (50) | 23.5 | 16 | −0.12 | S | 13 | 128 | +0.49 | R | 22 | 32 −0.16 | S |
| COLISTIN (8) | 15.5 | 8 | −0.76 | S | 16 | 16 | −0.73 | S | 13 | >128 −0.72 | R/S |
| CHLORAMPHENICOL (12.5) | 25.5 | 8 | +0.01 | S | 29.5 | 16 | −0.01 | S | 26.0 | 16 −0.12 | S |

ND = Not Done

TABLE 3

COMPARISON OF RESULTS OBTAINED BY ATP INDEX, AGAR DIFFUSION (KIRBY-BAUER), AND TUBE DILUTION MIC

| | MICROORGANISM | | | | | | | | | | |
|---|---|---|---|---|---|---|---|---|---|---|---|
| | Proteus mirabilis 04583 | | | | Pseudomonas aeruginosa 04275 | | | | Enterococcus 04390 | | |
| ANTIBIOTIC (μg/ml) | K-B (mm.) | MIC (μg/ml) | ATP INDEX | INTERPR. | K-B mm.) | MIC (μg/ml) | ATP INDEX | INTERPR. | K-B (mm.) | MIC (μg/ml) INDEX | INTERPR. |
| PENICILLIN G (8) | 20 | 2.5 | −0.10− +0.82 | S/S-R* | 0 | >80 | +0.84 | R | 18 | 2.5 −0.35 | S |
| AMPICILLIN (8) | 26.5 | 1.0 | +0.53 | S/R | 0 | >128 | +0.82 | R | 22 | 1.0 −0.54 | S |
| NAFCILLIN (0.6) | ND | ND | ND | ND | ND | ND | ND | ND | ND | ND ND | ND |
| CARBENICLLIN (128) | 30 | 2 | +0.10 | S | 19 | 128 | +0.68 | S/R | ND | ND ND | ND |
| CEPHALOTHIN (16) | 20 | 4 | −0.03 | S | 0 | >128 | +0.93 | R | 14 | 32 +0.78 | R |
| TETRACYCLINE (6) | 0 | 128 | +0.73 | R | 0 | 64 | +0.47 | R | 20 | 1.0 −0.04 | S |
| ERYTHROMYCIN (4) | 0 | >128 | +0.95 | R | 0 | >128 | +0.95 | R | 26 | <0.125 +0.18 | S |
| CLINDAMYCIN (2) | 0 | >128 | +0.99 | R | 0 | >128 | +0.90 | R | 0 | 8 +0.01 | R/S |
| GENTAMICIN (6) | 22 | 8 | +0.20 | S | 20.5 | 2 | −0.38 | S | 13 | 64 +0.88 | R |
| NITROFURANTOIN (50) | 11 | 128 | +0.45 | R | 0 | >128 | +0.98 | R | 23 | 8 +0.25 | S |
| COLISTIN (8) | 0 | >128 | +0.89 | R | 16 | 8 | −0.58 | S | 0 | <128 +0.69 | R |
| CHLORAMPHENICOL (12.5) | 28.0 | 4 | −0.15 | S | 14 | 64 | +0.46 | R | 22.0 | 8 −0.05 | S |

ND = Not Done

TABLE 4

| Antibiotic | Concentration (μg/ml) | Total Strains | Total (%) | | Major | Disagreement Falsely Resistant | Falsely Sensitive | Minor |
|---|---|---|---|---|---|---|---|---|
| AMPICILLIN | 8 | 69 | 13 | (19) | 13 | 12 | 1 | 0 |
| PENICILLIN G | 8 | 69 | 10 | (14) | 10 | 10 | 0 | 0 |
| | 0.075* | 18 | 1 | (5) | 1 | 1 | 0 | 0 |
| NAFCILLIN | 0.6 | 2 | 0 | (0) | 0 | 0 | 0 | 0 |
| CARBENICILLIN | 128 | 33 | 7 | (21) | 4 | 4 | 0 | 3 |
| CEPHALOTHIN | 16 | 82 | 4 | (5) | 4 | 3 | 1 | 0 |
| TETRACYCLINE | 6 | 81 | 7 | (9) | 2 | 1 | 1 | 5 |
| ERYTHROMYCIN | 4 | 77 | 4 | (5) | 0 | 0 | 0 | 4 |
| CLINDAMYCIN | 2 | 78 | 9 | (12) | 9 | 0 | 9 | 0 |
| GENTAMICIN | 6 | 81 | 0 | (0) | 0 | 0 | 0 | 0 |
| NITROFURANTOIN | 50 | 83 | 19 | (23) | 13 | 12 | 1 | 6 |
| COLISTIN | 8 | 81 | 2 | (2) | 2 | 0 | 2 | 0 |
| CHLORAMPHENICOL | 12.5 | 81 | 7 | (9) | 5 | 3 | 2 | 2 |

TABLE 4-continued

| Antibiotic | Concentration (μg/ml) | Total Strains | Total (%) | Major | Disagreement Falsely Resistant | Falsely Sensitive | Minor |
|---|---|---|---|---|---|---|---|
| | Total | 835 | 83 (10) | 63 | 46 | 17 | 20 |

*Staphylococcus aureus strains only

The overall comparison of the ATP index results of the present invention and the standard prior art agar diffusion test are shown in Table 4 under the column identified as "Disagreement". Of the total 83 (10%) instances of disagreement between the present ATP index technique and the agar diffusion technique, 3/4 of the disagreements were major, i.e., false resistance (43 of 63) readings or false sensitivity (17 of 63) readings. The other quarter of the disagreements were minor, i.e., intermediate results by the agar diffusion test and either sensitive (11 of 20) or resistant (9 of 20) by the ATP index test. The following is a detailed explanation of the disagreements shown.

this concentration, agreement was obtained in 17 of 18 instances. In Table 1, Penicillinase producing *S. aureus* frequently appeared to be penicillin sensitive after only a few hours of growth at 8 μg/ml because there was insufficient time for penicillinase induction to take place.

TABLE 5

Comparison of Staph. aureus sensitivity to penicillin G by agar diffusion, penicillinase production and the ATP index at varying concentrations of penicillin.

| Strain Number | Agar Diffusion: Zone Diameter in mm. | Interpretation | Penicillinase Production | 0.05 μg/ml | INT. | ATP Index Penicillin G Concentration 0.075 μg/ml | INT | 0.10 μg/ml | INT |
|---|---|---|---|---|---|---|---|---|---|
| ATCC No. 25923. | 32.5 | S | − | +0.29 | R | +0.04 | S | +0.08 | S |
| | 40 | S | − | 0.00 | S | −0.13 | S | −0.22 | S |
| | 37 | S | − | +0.12 | S | 0.01 | S | +0.02 | S |
| | 38.5 | S | − | +0.22 | S | +0.14 | S | +0.07 | R |
| | 37 | S | − | +0.58 | R | +0.57 | R | +0.42 | R |
| | 43 | S | − | +0.31 | R | +0.19 | S | +0.05 | S |
| | 18 | R | + | +0.70 | R | +0.85 | R | +0.40 | R |
| | 18.5 | R | + | +1.00 | R | +1.00 | R | +0.92 | R |
| | 20 | R | + | +0.66 | R | +0.53 | R | +0.28 | R |
| | 19 | R | + | +0.94 | R | +0.99 | R | +0.24 | S |
| | 17 | R | + | +0.99 | R | +0.94 | R | +0.93 | R |
| | 18 | R | + | +0.99 | R | +0.98 | R | +0.92 | S |
| | 22 | I | + | +0.87 | R | +0.62 | R | +0.75 | R |
| | 24.5 | I | + | +0.60 | R | +0.29 | R | +0.14 | S |
| | 25 | I | + | +0.49 | R | +0.38 | R | +0.04 | S |
| | 24 | I | + | +0.36 | R | +0.33 | R | +0.07 | S |
| | 23 | I | + | +0.84 | R | +0.71 | R | +0.45 | R |
| | 26.5 | I | + | +0.71 | R | +0.69 | R | +0.28 | R |

AMPICILLIN:

Twelve of the thirteen disagreements were obtained with the *Proteus* bacterial species (principally *P. mirabilis*). The discrepancies appeared because the strain appeared to be falsely resistant to ampicillin. An investigation showed that a decrease in the ATP content coincided with lysis of the organism by ampicillin (a cell-wall-active or β-lactam antibiotic), which lysis requires at least 3 hours after treatment with the antibiotic. Thus, the strain appeared falsely resistant. The false resistance readings can be corrected by incubating 3 hours.

PENICILLIN G:

The ten strains in disagreement occurred only with *Proteus mirabilis* which also appeared falsely resistant. As above, the false results were caused by a similar delay in the lysis of the *P. mirabilis* strains by Penicillin G.

The susceptibility results for *S. aureus* to Penicillin G represented unique difficulties. The problem was partially overcome by using lower concentrations of Penicillin G, such as 0.075 μg/ml as shown in Table 2. At

CARBENICILLIN:

Only the bacterial strains *E. coli*, *Proteus* and *P. aeuginosa* were studied for susceptibility because they were the only strains for which interpretive zone standards are available. Pseudomonas strains frequently exhibited false resistance because lysis of most pseudomonas strains by carbenicillin requires more than 6 hours.

CEPHALOTHIN:

Only four discrepancies were observed with cephalothin, of which three were false resistance readings with *P. mirabilis*. The false readings again reflect the delayed lysis observed in other instances with cell-wall active β-lactam antibiotics. The one false sensitivity exhibited by the Enterobacter strain is representative of the infrequent instance where several bacterial colonies are observed within the diffusion zone, despite an apparent zone inhibition in the susceptible range by agar diffusion. This result must be interpreted as a resistance showing, provided the purity of the strain can be confirmed which is a fact confirmed by MIC determinations. A rapid susceptibility technique is likely to show the strains as falsely sensitive because the majority of the bacterial population in the inoculum is, in fact, susceptible to cephalothin.

Only 7 disagreements were observed for tetracycline, and only two were major with no particular pattern. No major disagreements were observed for Erythromycin, and the four minor disagreements observed were confined to Enterococci which were sensitive by the ATP index and intermediate by the disc method.

CLINDAMYCIN:

All of the 9 disagreements observed were with Enterococci which were shown as sensitive by the ATP index and resistant by the (MIC) disc method. These discrepancies are explained by the fact that considerably sub-inhibitory concentrations, i.e., much less than the MIC method, of Clindamycin inhibit ATP synthesis during the first two hours of exposure, but thereafter ATP synthesis (and bacterial multiplication) progresses at a rate similar to that of the control. Consequently, an apparent lag appears before the ultimate resistance of the organism becomes apparent.

No disagreements were observed between the two compared methods for Gentamicin.

NITROFURANTOIN:

The results showed 19 disagreements, of which 6 were minor and 13 were major. False resistance readings occurred with Staphylococci and Enterococci for 12 of the 13 major disagreements. The ATP index in all instances was very close to the breakpoint value of +0.25. Studies showed that the inhibition of *S. aureus* by nitrofurantoin was not apparent until one hour after incubation. Because of the relatively slower growth of the control organism compared to gram-negative organisms, the prerequisite index for sensitivity cannot be achieved even in 3 hours. The problem could be solved by applying different interpretive criteria to this drug, i.e., a breakpoint ATP index of +0.35.

COLISTIN:

False sensitivity readings were obtained in two instances for Enterobacter-Serratia strains. These results were attributable to an apparent zone of inhibition in the sensitive range for agar diffusion, but several bacterial colonies were observed within the zones. This fact lead to the necessity of a resistance interpretation.

Seven disagreements were observed for chloramphenicol, of which five were major and two were minor. The discrepancies were distributed in no particular pattern among several species.

Table 6 shows the agreement between technologists conducting the same ATP index operations. The same overall agreement results with the agar diffusion method were obtained. A 94% agreement was obtained between technologists.

The results obtained by the present ATP index method of testing microbial susceptibility to certain antibiotics gives a 90% correlation with the standard agar diffusion method. This figure compares favorably with existing laboratory methods which have undergone extensive laboratory evaluation.

The principles, preferred embodiments, and modes of operation of the present invention have been described in the foregoing specification. The invention which is intended to be protected herein, however, is not to be construed as limited to the particular forms disclosed since these are to be regarded as illustrative rather than restrictive. Variations and changes may be made by those skilled in the art without departing from the spirit of the present invention.

What is claimed is:

1. A method for determining the sensitivity of bacteria to antimicrobial agents by measurement of the ATP index indicating sensitivity, which comprises:
   culturing bacterium in a growth medium;
   developing a uniform inoculum;
   preincubating the inoculum for a period sufficient to initiate growth;
   aliquoting at least three test portions, at least one test portion having an antibiotic added and at least two test portions without antibiotic added;
   assaying the amount of bacterial adenosine triphosphate in the test portions, one assay on a test portion without antibiotic being made prior to any incubation, the other assays being made after incubation;
   determining the ATP index to indicate sensitivity of the bacterium to the antibiotic;
   the ATP index being determined according to the formula:

$$\text{ATP index} = B_t - A_o / A_t - A_o,$$

where
   $B_t$ represents a light reading for a test portion treated with antibiotic and allowed to incubate for a time $t$;
   $A_t$ represents a light reading for a test portion not treated with antibiotic and allowed to incubate for a time $t$; and
   $A_o$ represents a light reading for a test portion not treated with antibiotic and which is not allowed to incubate, at time zero.

2. The method of claim 1 wherein said bacterium is derived from a body fluid selected from the group consisting of urine, ascites, lymph fluid, plasma, blood, spinal fluid, saliva and mucus.

3. The method of claim 1 wherein the culturing is for a period of from 8 to 96 hours at 20° to 45° C and at least one bacterial colony is then isolated and further cultured for a period of from 16 to 48 hours.

TABLE 6

| | Reproducability of the ATP Index | | | |
|---|---|---|---|---|
| Antibiotic | No. strains tested | Major disagreements with agar diffusion | | Disagreements between Tech-1 and Tech-2 |
| | | Tech-1 | Tech-2 | |
| Ampicillin | 8 | 2 | 3 | 1 |
| Penicillin G | 8 | 0 | 0 | 0 |
| Carbenicillin | 4 | 0 | 0 | 0 |
| Cephalothin | 10 | 0 | 0 | 0 |
| Tetracycline | 10 | 0 | 0 | 1 |
| Erythromycin | 10 | 0 | 0 | 0 |
| Clindamycin | 10 | 0 | 0 | 0 |
| Gentamicin | 10 | 1 | 0 | 1 |
| Nitrofurantoin | 10 | 2 | 2 | 1 |
| Colistin | 10 | 1 | 0 | 1 |
| Chloramphenicol | 10 | 2 | 3 | 1 |
| TOTAL | 100 | 8 | 8 | 6 |

4. The method of claim 1 wherein the uniform inoculum is developed by obtaining a broth culture of from about $10^4$ CFU/ml to about $10^8$ CFU/ml.

5. The method of claim 4 wherein the uniform inoculum is about $10^6$ CFU/ml.

6. The method of claim 1 wherein preincubation takes place at a temperature of from 20° to 45° C.

7. The method of claim 1 wherein assaying the amount of bacterial adenosine triphosphate in the test portions involves assaying at least one portion without antibiotic prior to incubation and, thereafter, assaying at least one portion with antibiotic and at least one portion without antibiotic after incubation at a temperature of from 20° to 45° C for a period of from 0.5 to 10 hours.

8. A method for determining the sensitivity of bacteria to antimicrobial agents by measurement of the ATP index indicating sensitivity, which comprises:
   culturing bacterium in a growth medium;
   developing a uniform inoculum;
   preincubating the inoculum for a period sufficient to initiate growth;
   aliquoting at least three test portions, at least one test portion having an antibiotic added and at least two test portions without antibiotic added;
   assaying the amount of bacterial adenosine triphosphate in the test portions, one assay on a test portion without antibiotic being made prior to any incubation;
   determining the ATP index to indicate sensitivity of the bacterium to the antibiotic,
   the ATP index being determined according to the formula:

$$\text{ATP index} = \log B_t - \log A_o / \log A_t - \log A_o,$$

where
   $B_t$ represents a light reading for a test portion treated with antibiotic and allowed to incubate for a time $t$;
   $A_t$ represents a light reading for a test portion not treated with antibiotic and allowed to incubate for a time $t$; and
   $A_o$ represents a light reading for a test portion not treated with antibiotic and which is not allowed to incubate, at time zero.

9. The method of claim 8 wherein said bacterium is derived from a body fluid selected from the group consisting of urine, ascites, lymph fluid, plasma, blood, spinal fluid, saliva and mucus.

10. The method of claim 8 wherein the culturing is for a period of from 8 to 96 hours at 20° to 45° C and at least one bacterial colony is then isolated and further cultured for a period of from 16 to 48 hours.

11. The method of claim 8 wherein the uniform inoculum is developed by obtaining a broth culture of from about $10^4$ CFU/ml to about $10^8$ CFU/ml.

12. The method of claim 11 wherein the uniform inoculum is about $10^6$ CFU/ml.

13. The method of claim 8 wherein preincubation takes place at a temperature of from 20° to 45° C.

14. The method of claim 8 wherein assaying the amount of bacterial adenosine triphosphate in the test portions involves assaying at least one portion without antibiotic prior to incubation and, thereafter, assaying at least one portion with antibiotic and at least one portion without antibiotic after incubation at a temperature of from 20° to 45° C for a period of from 0.5 to 10 hours.

15. A method for determining the sensitivity of bacteria to antimicrobial agents by measurement of the ATP index indicating sensitivity, which comprises:
   culturing bacterium in a growth medium from 8 to 96 hours at 20° to 45° C and at least one bacterial colony is then isolated and further cultured for a period of from 16 to 48 hours;
   developing a uniform inoculum by obtaining a broth culture of about $10^6$ CFU/ml;
   preincubating the inoculum for a period sufficent to initiate growth at a temperature from 20° to 45° C;
   aliquoting test portions of the culture by separation into at least three test portions, at least one test portion having an antibiotic added and at least two test portions without antibiotic added;
   assaying the amount of bacterial adenosine triphosphate in the test portions, using an ATP-luciferase technique, by assaying at least one portion without antibiotic prior to incubation and, thereafter, assaying at least one portion with antibiotic and at least one portion without antibiotic after incubation at a temperature of from 20° to 45° C for a period of from 0.5 to 10 hours; and
   determining the ATP index to indicate sensitivity of the bacterium to the antibiotic according to the formula:

$$\text{ATP index} = B_t - A_o / A_t - A_o,$$

where
   $B_t$ represents a light reading for a test portion treated with antibiotic and allowed to incubate for a time $t$;
   $A_t$ represents a light reading for a test portion not treated with antibiotic and allowed to incubate for a time $t$; and
   $A_o$ represents a light reading for a test portion not treated with antibiotic and which is not allowed to incubate, at time zero.

* * * * *